(12) United States Patent
Pulaski et al.

(10) Patent No.: US 10,849,495 B2
(45) Date of Patent: *Dec. 1, 2020

(54) SYSTEMS AND METHODS OF OPTICAL COHERENCE TOMOGRAPHY WITH A MULTI-FOCAL DELAY LINE

(71) Applicant: AMO Development, LLC, Santa Ana, CA (US)

(72) Inventors: Paul Pulaski, Albuquerque, NM (US); Daniel R. Neal, Tijeras, NM (US); Thomas D. Raymond, Edgewood, NM (US); Stephen W. Farrer, Albuquerque, NM (US); Daniel R. Hamrick, Cedar Crest, NM (US); Richard J. Copland, Albuquerque, NM (US)

(73) Assignee: AMO Development, LLC, Santa Ana, CA (US)

( * ) Notice: Subject to any disclaimer, the term of this patent is extended or adjusted under 35 U.S.C. 154(b) by 65 days.

This patent is subject to a terminal disclaimer.

(21) Appl. No.: 16/148,950

(22) Filed: Oct. 1, 2018

(65) Prior Publication Data

US 2019/0029512 A1 Jan. 31, 2019

Related U.S. Application Data

(63) Continuation of application No. 14/968,615, filed on Dec. 14, 2015, now Pat. No. 10,085,634.

(Continued)

(51) Int. Cl.
*A61B 3/10* (2006.01)
*A61B 3/00* (2006.01)
*G02B 6/12* (2006.01)

(52) U.S. Cl.
CPC ............ *A61B 3/102* (2013.01); *A61B 3/0025* (2013.01); *A61B 3/1005* (2013.01);
(Continued)

(58) Field of Classification Search
CPC ..... A61B 3/102; A61B 3/0025; A61B 3/1005; A61B 5/0073; A61B 5/04001;
(Continued)

(56) References Cited

U.S. PATENT DOCUMENTS 5,777,719 A  7/1998 Williams et al.
6,550,917 B1  4/2003 Neal et al.
(Continued)

OTHER PUBLICATIONS

International Search Report and Written Opinion for Application No. PCT/US2015/065612, dated Mar. 7, 2016, 11 pages.

*Primary Examiner* — Mustak Choudhury
(74) *Attorney, Agent, or Firm* — Johnson & Johnson Surgical Vision, Inc.

(57) ABSTRACT

An optical coherence tomography (OCT) system includes: a light source; a multi-focal delay line; and a light detector. The multi-focal delay line includes: a positive lens; and an optical switch configured to: receive a light from the light source; selectively direct the sample light to the positive lens via a selected one of a plurality of light interfaces each located a different distance from the focal plane of the positive lens; and direct the sample light to an object to be measured. The light detector is configured to receive return light returned from the object to be measured in response to the sample light, and to receive a reference light produced from the light from the light source, and in response thereto to detect at least one interference signal. An associated OCT method may be performed with the OCT system.

23 Claims, 13 Drawing Sheets

Related U.S. Application Data

(60) Provisional application No. 62/113,196, filed on Feb. 6, 2015.

(52) U.S. Cl.
CPC ............... *G02B 6/12004* (2013.01); *G02B 2006/12145* (2013.01); *G02B 2006/12159* (2013.01)

(58) Field of Classification Search
CPC ............. A61B 5/0066; G01N 21/4795; G01B 6/12004; G01B 9/02091; G01B 9/02016; G01B 9/02028; G01B 9/02007; G01B 9/02027; G01B 9/02044; G01B 9/02021; G01S 7/5206; G10K 11/346
USPC ............ 351/205–221; 72/620, 625; 356/479, 356/492, 497; 600/443
See application file for complete search history.

(56) References Cited

U.S. PATENT DOCUMENTS

| | | | | |
|---|---|---|---|---|
| 2011/0279821 A1* | 11/2011 | Brennan | ............... | A61B 3/102 356/479 |
| 2013/0301006 A1* | 11/2013 | Kim | ................... | G01B 9/02027 351/206 |

\* cited by examiner

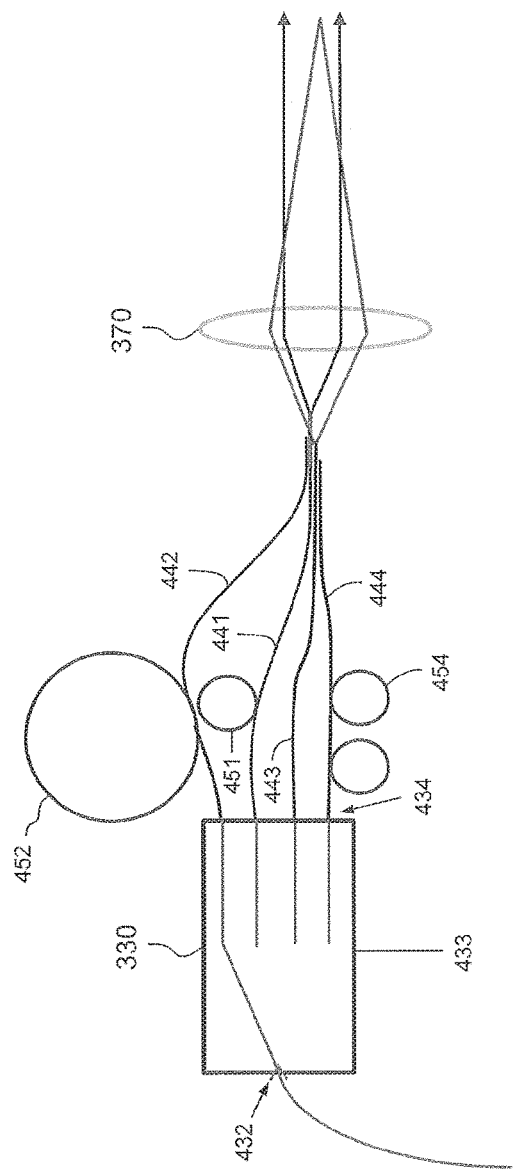

SYSTEMS AND METHODS OF OPTICAL COHERENCE TOMOGRAPHY WITH A MULTI-FOCAL DELAY LINE

RELATED APPLICATIONS

This application is a continuation of and claims priority to U.S. patent application Ser. No. 14/968,615, filed on Dec. 14, 2015, and also claims the benefit under 35 U.S.C. § 119(e) of U.S. Provisional Application Ser. No. 62/113,196, filed Feb. 6, 2015, both of applications are incorporated herein in their entirety by reference.

BACKGROUND

Field

This invention generally pertains to the field of vision diagnostics, and in particular, to a method and system for objectively measuring an optical characteristic of an eye.

DESCRIPTION

Optical coherence tomography (OCT) is an established imaging technique that uses light to capture micrometer-resolution, three-dimensional images from within optical scattering media, including for example, biological tissue. OCT is based on low-coherence interferometry that typically employs near-infrared light. Using relatively long wavelength light allows the light to penetrate into the scattering medium. Depending on the properties of the light source, OCT can achieve sub-micrometer resolution (with very wide-spectrum sources emitting over a ~100 nm wavelength range).

OCT has applications in ophthalmology, where it can be used to obtain detailed images of different features of the eye.

OCT may be employed in an optical measurement instrument, which performs cataract diagnostics or pre-operational cataract treatment planning that may include specification and/or selection of an appropriate intraocular lens (IOL) for a particular patient, and/or post-surgical test and evaluation after an IOL has been implanted, etc.

Typically, to measure the entire eye, existing OCT instruments adjust the collimation/focusing in the sample arm of the interferometer to obtain optimum return signals from the different elements or regions of the eye. For example, the best corneal return signals are obtained when the sample light is focused on the cornea, while the best retinal return signals are obtained when the sample light is focused on the retina. Additionally, the time delay between the sample optical path and the reference optical path must be adjusted for the different regions of the eye for OCT instruments having a depth range of less than 50 mm in air. Additionally, in an eye measurement instrument where the eye is not physically constrained, the measurements of all regions and elements of the eye should be measured within a very short time of each other (e.g., within a total time period of 80 msec.) so as to avoid the possibility of eye movement that may diminish or degrade the quality or accuracy of the measurements.

Currently, OCT instruments typically either adjust the collimation/focus by means of a lens that is translated along the optical axis of the instrument (e.g., using a linear motor or voice coil type actuator), or change the focal length of a lens through electro-optic or "liquid lens" technology. Of the translation devices, linear motor translators are slow, requiring fractions of a second, and therefore, are highly susceptible to eye movement during the measurements. The voice coil type actuators can translate the lens in a time frame on the order of 10 msec, but they are generally expensive. Electro-optic lenses can be adjusted sufficiently rapidly, but they are expensive and not always compatible with the wide optical bandwidth required for an OCT instrument. Liquid lenses can be quite economical, but are generally not thermally stable, can introduce aberrations that affect the return signal from the eye and typically can not be built to have effective anti-reflection coatings on the liquid interfaces.

Therefore, it would be desirable to provide a system and method for optical coherence tomography (OCT) which can support relatively rapid OCT measurements in a cost effective manner. In particular, it would be desirable to provide a cost effective system and method for optical coherence tomography (OCT) which can support measurements of an entire human eye within a timeframe which minimizes difficulties associated with a subject's movement of the eye during a measurement interval.

SUMMARY OF THE INVENTION

Hence, to obviate one or more problems due to limitations or disadvantages in the related art, this disclosure provides embodiments including a system comprising: a light source configured to emit light; a first optical system configured to receive the light from the light source and to produce therefrom reference light and sample light; a reference optical path configured to receive the reference light from the first optical element; a multi-focal delay line, comprising: an optical switch configured to receive the sample light from the first optical system and to selectively couple the sample light to a selected light interface among a plurality of light interfaces, and a positive lens system, wherein the light interfaces are all separated and spaced apart from the positive lens system and located at different distances than each other from an effective focal plane of the positive lens, wherein the positive lens system is configured to receive the sample light from the selected light interface, to provide the sample light to an eye, to receive return light from the eye, and to provide the return light to the selected light interface, wherein the optical switch is further configured to provide the return light to the first optical system; a light detector configured to receive the reference light from the reference optical path, and to receive the return light from the first optical system, and in response thereto to detect at least one interference signal; and one or more processors configured to control the optical switch to selectively couple the sample light to each of the plurality of light interfaces, one at a time, and further configured to measure at least one characteristic of the eye from the detected interference signal when the sample light is selectively coupled to the plurality of light interfaces. The signal may be a spatial distribution of light and dark fringes on a detector array for a spectral domain OCT system. Or, the signal may be a time varying voltage from balanced photodetectors for a swept source OCT system.

In some embodiments, the optical switch has a plurality of output ports, and the multi-focal delay line includes a plurality of optical waveguides each connected to one of the output ports, the plurality of optical waveguides providing the plurality of light interfaces.

In some versions of these embodiments, each of the light interfaces comprises a second end of a corresponding one of the optical waveguides.

In some versions of these embodiments, the system further comprises an integrated optical circuit including the optical switch, an adjustable optical delay, and the optical waveguides.

In some embodiments, the optical switch has a plurality of output ports, and wherein the multi-focal delay line comprises a plurality of optical fibers each having a first end coupled to one of the plurality of output ports, and wherein each of the light interfaces comprises a second end of a corresponding one of the optical fibers.

In some versions of these embodiments, each of the optical fibers has a different length.

In some embodiments, the one or more processors are further configured to determine at least one distance between two different components of the eye from the detected interference signal when the sample light is selectively coupled to the light interfaces.

In some versions of these embodiments, the distances include at least one of: a distance between a reference plane and the anterior surface of a cornea, a distance between a surface of a cornea and a surface of a lens, a distance between a surface of the lens and a retina; and a distance between a surface of the cornea and the retina.

In some embodiments, the optical system includes at least one scanning device configured to scan the sample light on the eye in at least one direction.

In some embodiments, at least one of the light interfaces is distanced from the positive lens so that the sample light provided from the optical system to the eye is substantially focused on the retina.

In some versions of these embodiments, at least another one of the light interfaces is distanced from the positive lens so that the sample light provided from the optical system to the eye is substantially focused on a cornea of the eye.

In some versions of these embodiments, at least another one of the light interfaces is distanced from the positive lens so that the sample light provided from the optical system to the eye is substantially focused on a lens of the eye.

In some embodiments, the light produced by the light source has a coherence length, and wherein the light interfaces are arranged with respect to the focal plane of the positive lens system such that the return light from the eye for a first one of the light interfaces principally comes from a first depth in the eye and the return light from the eye for a second one of the light interfaces principally comes from a second depth in the eye different from the first depth, and wherein a distance between the first depth and the second depth is greater than the coherence length.

In some versions of these embodiments, the system is further configured to automatically change a delay provided by the multi-focal delay line to match each of the first and second depths when the light is output from the first one of the light interfaces and the second one of the light interfaces, respectively.

In some embodiments, the light interfaces are all disposed within three degrees of an optical axis of the positive lens.

In some embodiments, the first optical system includes a beam splitter configured to receive the light from the light source and to produce therefrom the reference light and the sample light.

In some embodiments, the first optical system includes a fiber optical coupler configured to receive the light from the light source and to produce therefrom the reference light and the sample light.

In another aspect of the invention, a method comprises: producing sample light and reference light from a common light source; controlling an optical switch to direct the sample light to an eye via a first selected light interface and a positive lens; detecting at least one first interference signal from the reference light and return light returned from the eye in response to the sample light being directed to the eye via the first selected light interface; controlling the optical switch to direct the sample light to the eye via a second selected light interface and the positive lens, wherein the second selected light interface is disposed at a different distance from a focal plane of the positive lens than the first selected light interface; detecting at least one second interference signal from the reference light and return light returned from the eye in response to the sample light being directed to the eye via the second selected light interface; and determining at least one distance between at least two different features of the eye from the detected first and second interference signal.

In some embodiments, the first selected light interface is distanced from the positive lens so that the sample light provided to the eye is substantially collimated.

In some versions of these embodiments, the second selected light interface is distanced from the positive lens so that the sample light is focused on a cornea of the eye.

In some versions of these embodiments, the method further includes determining a distance between the cornea and a retina of the eye from the detected first and second interference signal.

In some versions of these embodiments, the method further includes scanning the sample light in at least one direction so as to create a plurality of first interference signals from the reference light and return light returned from the eye in response to the sample light being directed to the eye via the first selected light interface and to create a plurality of second interference signals from the reference light and return light returned from the eye in response to the sample light being directed to the eye via the second selected light interface.

In yet another aspect of the invention, a system comprises: a light source; a multi-focal delay line, comprising: a positive lens having a focal plane, and an optical switch configured to receive a light from the light source and to selectively direct the sample light to the positive lens via a selected one of a plurality of light interfaces each located a different distance from the focal plane of the positive lens, wherein the positive lens is further configured to direct the sample light to an object to be measured; and a light detector configured to receive the return light returned from the object to be measured in response to the sample light being directed to the object to be measured via the positive lens, and to receive a reference light produced from the light from the light source, and in response thereto to detect at least one interference signal.

In some embodiments, the system further includes a controller configured to: control the optical switch to direct the sample light to the positive lens via a first one of the plurality of light interfaces to create at least one first interference signal from the reference light and return light returned from the object to be measured in response to the sample light being directed to the object to be measured via the first light interface; control the optical switch to direct the sample light to the positive lens via a second one of the plurality of light interfaces to create at least one second interference signal from the reference light and return light returned from the object to be measured in response to the sample light being directed to the object to be measured via the second light interface; and determine at least one distance between at least two different features of the object to be measured from the first and second interference signal.

In some embodiments, the multi-focal delay line further comprises: a plurality of optical couplers, each optical coupler including: a first port coupled to an output of the optical switch, a second port coupled to a corresponding return light input of the light detector, a third port coupled to a corresponding one of the plurality of light interfaces, and a fourth port; and a plurality of reference optical paths each coupled between the fourth port of a corresponding one of the plurality of optical couplers and a corresponding reference light input of the light detector.

In some embodiments, the multi-focal delay line further comprises: a plurality of optical couplers, each optical coupler including: a first port coupled to an output of the optical switch, a second port coupled to a first light input of the light detector, a third port coupled to a corresponding one of the plurality of light interfaces, and a fourth port; and a plurality of reference optical paths each coupled between the fourth port of a corresponding one of the plurality of optical couplers and a second light input of the light detector.

In some versions of these embodiments, the system further comprises: a first optical combiner having a plurality of inputs each of which is coupled to the second port of a corresponding one of the plurality of optical couplers, and having an output coupled to the first light input of the light detector; and a second optical combiner having a plurality of inputs each of which is coupled to on output of a corresponding one of the plurality of reference optical paths, and having an output coupled to the second light input of the light detector.

In some versions of these embodiments, the system further comprises: a second optical switch having a plurality of inputs each of which is coupled to the second port of a corresponding one of the plurality of optical couplers, and having an output coupled to the first light input of the light detector; and a third optical switch having a plurality of inputs each of which is coupled to on output of a corresponding one of the plurality of reference optical paths, and having an output coupled to the second light input of the light detector.

This summary and the following detailed description are merely exemplary, illustrative, and explanatory, and are not intended to limit, but to provide further explanation of the invention as claimed. Additional features and advantages of the invention will be set forth in the descriptions that follow, and in part will be apparent from the description, or may be learned by practice of the invention. The objectives and other advantages of the invention will be realized and attained by the structure particularly pointed out in the written description, claims and the appended drawings.

BRIEF DESCRIPTION OF THE DRAWINGS

The novel features of the invention are set forth with particularity in the appended claims. A better understanding of the features and advantages of the present invention will be obtained by referring to the following detailed description that sets forth illustrative embodiments using principles of the invention, as well as to the accompanying drawings of which:

FIGS. 4A and 4B illustrate one embodiment of a multi-focal delay line (MFDL) that may be included in an optical coherence tomographer.

DETAILED DESCRIPTION

The following description describes various embodiments of the present invention. For purposes of explanation, specific configurations and details are set forth so as to provide a thorough understanding of the embodiments. It will also, however, be apparent to one skilled in the art that embodiments of the present invention can be practiced without certain specific details. Further, to avoid obscuring the embodiment being described, various well-known features may be omitted or simplified in the description.

It would be desirable to incorporate an OCT system into an eye instrument for cataract diagnostics that also measures the refractive state of an eye. Such a system may use a method of operation that can draw the eye into its farthest possible refractive state when measurements are made, while also maintaining a large pupil size for both younger subjects and older subjects.

As used herein, the term "light source" means a source of electromagnetic radiation, particularly a source in or near the visible band of the electromagnetic spectrum, for example, in the infrared, near infrared, or ultraviolet bands of the electromagnetic radiation. As used herein, the term "light" may be extended to mean electromagnetic radiation in or near the visible band of the electromagnetic spectrum, for example, in the infrared, near infrared, or ultraviolet bands of the electromagnetic radiation.

Figure 1:
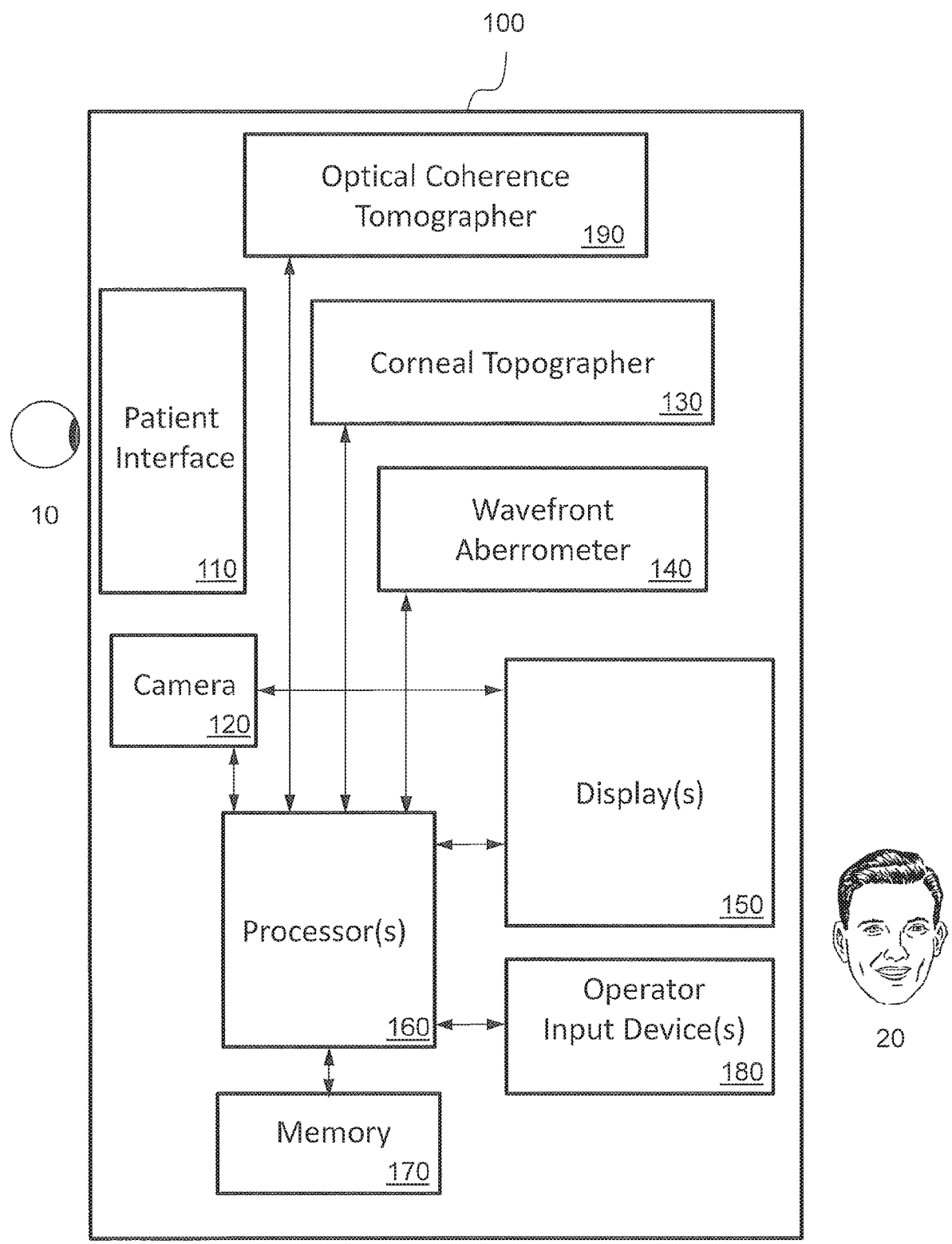
FIG. 1 is a functional block diagram of one embodiment of an optical measurement system.

FIG. 1 is a functional block diagram of one embodiment of an optical measurement instrument or optical measurement system 100 for measuring one or more characteristics of an eye 10. Optical measurement system 100 includes a patient interface (e.g., a headrest and eye examination area), a camera 120, a corneal topographer 130, a wavefront aberrometer 140, one or more displays 150, one or more processors 160 and associated storage (e.g., memory) 170, one or more operator input devices 180 for receiving input or instructions from an operator 20, and an optical coherence tomography (OCT) subsystem 190. It should be understood that optical measurement system 100 is simply one embodiment for illustrating principles of the invention, and that many variations are possible which may omit certain elements, add additional elements, and/or change some of the elements. Some implementations may include additional elements not specifically shown in FIG. 1.

In some implementations, camera 120 may be an eye alignment camera which is used to insure proper eye alignment when making corneal topography, wavefront aberrometry measurements, and/or optical coherence tomography measurements with corneal topographer 130, wavefront aberrometer 140, and/or OCT subsystem 190. Beneficially, camera 120 alone or in conjunction with processor(s) 160 may provide a continuous live display of eye 10 to operator 20 via display 150.

Wavefront aberrometer 140 may measure wavefront aberrations of eye 10 from which one or more optical characteristics may be ascertained. As described in greater detail below with respect to FIGS. 2A-B, wavefront aberrometer 140 includes a fixation target for the subject to view when measurements are made of eye 10.

Although example configurations of corneal topographer 130 and wavefront aberrometer 140 will be described in further detail below with respect to FIG. 2A-B, it should be understood that these elements may employ any of a variety of other configurations.

Display(s) 150 may include one or more display devices which provide images and/or data to operator 20 under control of processor(s) 160. Such images and data may include operating instructions and/or requests for input from operator 20, images of eye 20 produced by camera 120, images and data reflecting measurements of eye 10 performed by corneal topographer 130, wavefront aberrometer 140, OCT subsystem 190, etc. Display(s) 150 may include one or more flat panel displays, including one or more touchscreens, individual lights (e.g., light emitting diodes), or any other convenient display device(s).

Processor(s) 160 execute(s) computer-readable instructions for performing operations of optical measurement system 100. Such operations may include: adjusting one or more operating parameters of corneal topographer 130, wavefront aberrometer 140, and/or OCT subsystem 190; processing data output by corneal topographer 130, wavefront aberrometer 140, and/or OCT subsystem 190 interpreting and responding to inputs and/or instructions received by operator input device(s) 180; generating images and/or data for display by display(s) 150; etc. In particular, as described in greater detail below, processor(s) 160 may control or adjust a brightness level of a fixation target employed by optical measurement system 100, for example as part of wavefront aberrometer 140. Processor(s) 160 may perform into operations using instructions and/or data stored in associated storage 170. Storage 170 may include any combination of volatile memory devices (e.g., random access memory), nonvolatile memory devices (e.g., read only memory, FLASH memory), computer readable media such as hard disk drives, optical disks, etc. In particular, storage 170 may store an operating system for processor(s) 160 and one or more computer programs which are executed by processor(s) 160 during operation of optical measurement system 100. In some implementations, storage 170 may store computer-readable instructions which cause processor(s) 160 to execute one or more algorithms for making wavefront measurements of a subject's eye 10. In some implementations, storage 170 may store computer-readable instructions which cause processor(s) 160 to execute one or more algorithms described below, for example with respect to FIG. 11. In some implementations, storage 170 may store raw data produced by corneal topographer 130, wavefront aberrometer 140, and/or OCT subsystem 190, and/or data from corneal topographer 130, wavefront aberrometer 140, and/or OCT subsystem 190 which has been processed by processor(s) 160.

Operator input device(s) 180 may include any combination of the following devices: keyboard, touchscreen, touchpad, joystick, pushbuttons, roller ball, mouse, keypad, microphone, etc.

In general, processor(s) 160 operate in conjunction with display(s) 150 and operator input device(s) 180 to provide a user interface for receiving instructions and data from operator 20 and for communicating warnings, instructions, and data to operator 20. These warnings may indicate to the operator when the quality of the signal data is deficient in some manner and that the data should re-collected. For example, the fringe visibility (ratio of dark to light in the signal) might be low so the data should be re-collected. In another case, the fringe visibility itself may be good, but other conditions may exist that indicate the data should not be relied upon. For instance, the corneal topography data may indicate poor tear film was present during the measurement, so the data should be recollected. In another example, the gaze of the patient may have wandered so the data should be recollected. In a combined instrument including corneal topography, iris imaging, wavefront sensor, and OCT, there are a number of combinations of comparisons and correlations that may be performed to indicate if a data set is good. Whether such relationships are good may be summarized by a data quality indicator. One use of such an indicator would be to guide an instrument operator regarding the measurement should be redone. Another use would be to provider an indicator to the doctor reviewing the data later to help him or her understand if the data is reliable for use.

Figure 2A:
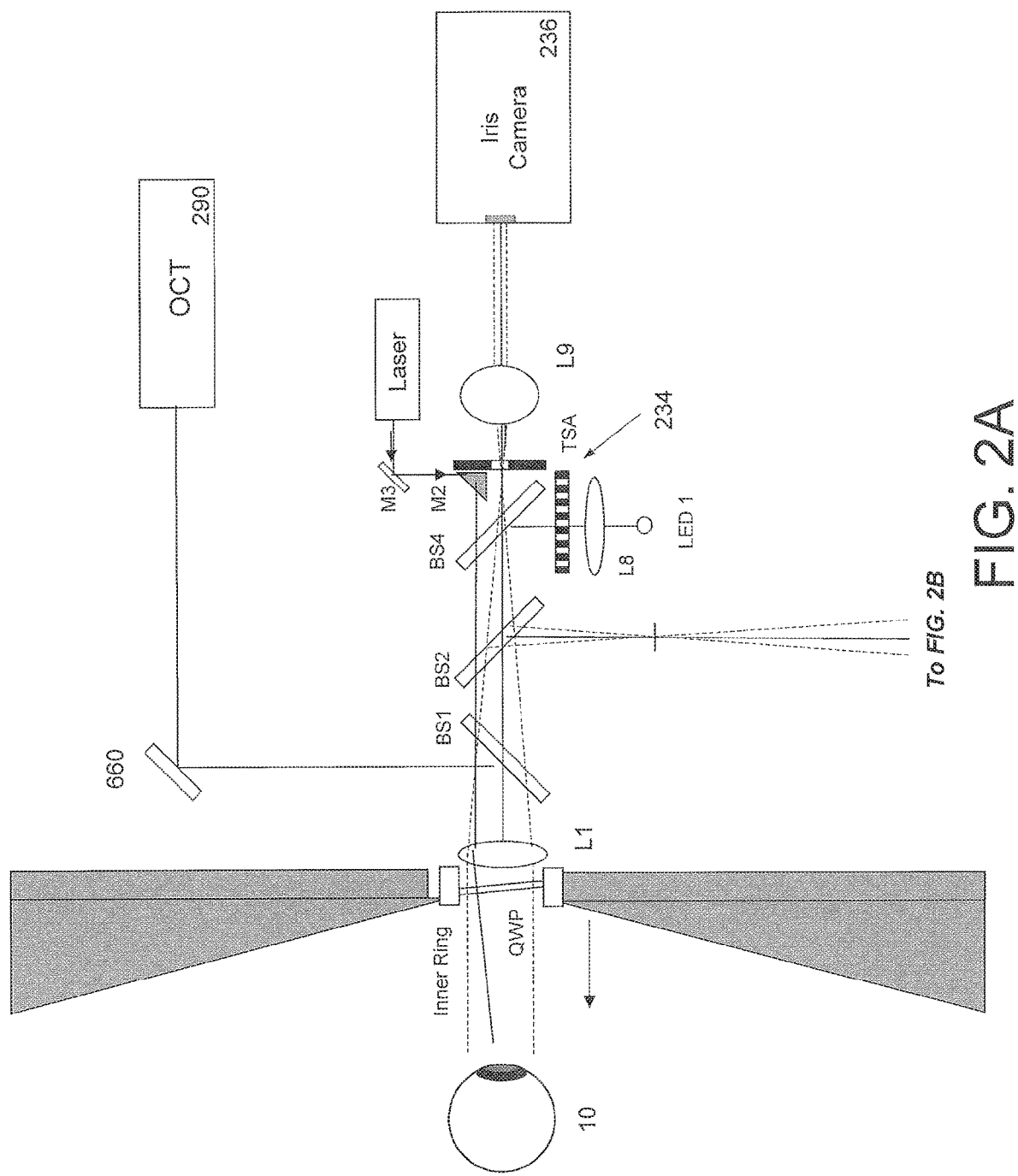
FIGS. 2A and 2B combine to form a more detailed diagram of portions of one embodiment of an optical measurement system.
Figure 2B:
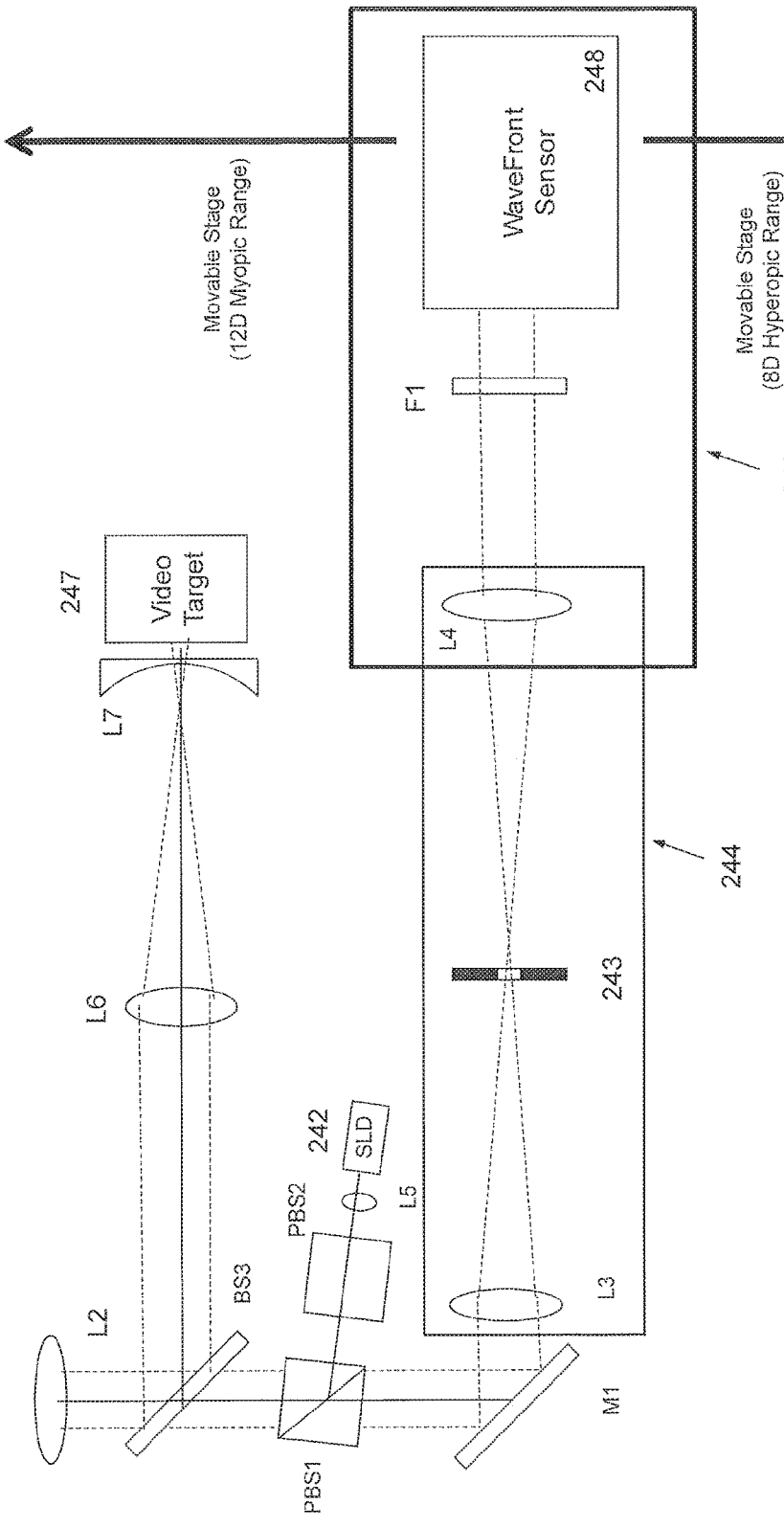

FIGS. 2A and 2B combine to form a more detailed diagram of portions of one embodiment of an optical measurement system 200. Optical measurement system 200 may be one embodiment of optical measurement instrument 100 according to the block diagram of FIG. 1. In particular, FIG. 2A shows elements of an optical coherence tomographer subsystem, such as optical coherence tomographer subsystem 190 of FIG. 1, and elements of a corneal topographer subsystem, such as corneal topographer subsystem 130 of FIG. 1. FIG. 2B shows elements of a wavefront aberrometer subsystem, such as wavefront aberrometer 140 of FIG. 7, and a fixation target.

In particular, FIG. 2A shows an optical coherence tomography (OCT) subsystem 290 and scanning mirrors 660. As discussed in greater detail below, OCT subsystem 290 can be controlled (e.g., by processor(s) 160) to selectively focus the OCT measurements at different parts of a subject's eye (e.g., anterior corneal surface; posterior corneal surface; anterior lens surface; posterior lens surface; retinal surface; etc.).

FIG. 2A also shows a corneal topographer subsystem with an inner ring light source and Helmholtz sources formed by an LED 1, a diffuser lens L8, and a plate 234 with holes for passing the diffused light therethrough. FIG. 2A also shows an iris camera 236. FIG. 2A shows various other optical elements such as: beam splitters BS1, BS2, BS4; lenses L1, L8 and L9; a quarter-wave plate QWP; mirrors M2 and M3; a laser and an LED1.

FIG. 2B shows a wavefront aberrometer subsystem, including a wavefront sensor 248 and an adjustable telescope 244 with a dynamic range limiting aperture 233 disposed between the lenses L3 and L4 of adjustable telescope 244. Beneficially, wavefront sensor 248 and one of the telescope lenses (e.g., L4) may be mounted on a movable stage 246 which can be adjusted to correct, for example, for up to 12 Diopters in the myopic range and up to 8 Diopters in the hyperopic range. FIG. 2B also shows a superluminescent diode (SLD) as a light source 242 for the wavefront aberrometer, and a fixation target in the visible light range, for example a video target 247.

In some embodiments, various subsystems of optical measurement instrument 200 may operate with light at different wavelengths. For example, in some embodiments: the optical coherence topographer subsystem may operate with light at a wavelength of about 1060 nm; the Helmholtz sources of the corneal topographer subsystem may operate at a wavelength of about 760 nm; the iris camera may use light at both 760 nm of the Helmholtz sources and at 950 nm; fixation target 247 may operate in a visible wavelength range of 500-600 nm; and wavefront sensor 248 may operate at a wavelength of about 840 nm.

Beneficially, wavefront sensor 248 may be Shack-Hartmann wavefront sensor comprising a detector array and a plurality of lenslets for focusing received light onto its detector array. In that case, the detector array may be a CCD, a CMOS array, or another electronic photosensitive device. Embodiments of wavefront sensors which may be employed in one or more systems described herein are described in U.S. Pat. No. 6,550,917, issued to Neal et al. on Apr. 22, 2003, and U.S. Pat. No. 5,777,719, issued to Williams et al. on Jul. 7, 1998, both of which patents are hereby incorporated herein by reference in their entirety. However, other wavefront sensors may be employed instead.

Wavefront sensor 248 outputs signals to processor(s) 160 which use(s) the signals to determine ocular aberrations of eye 10. Beneficially, processor(s) 160 is/are able to better characterize eye 10 by considering the corneal topography of eye 10, which may also be determined by processor(s) 160 based on outputs of detector array 1400, as explained above.

Figure 3:
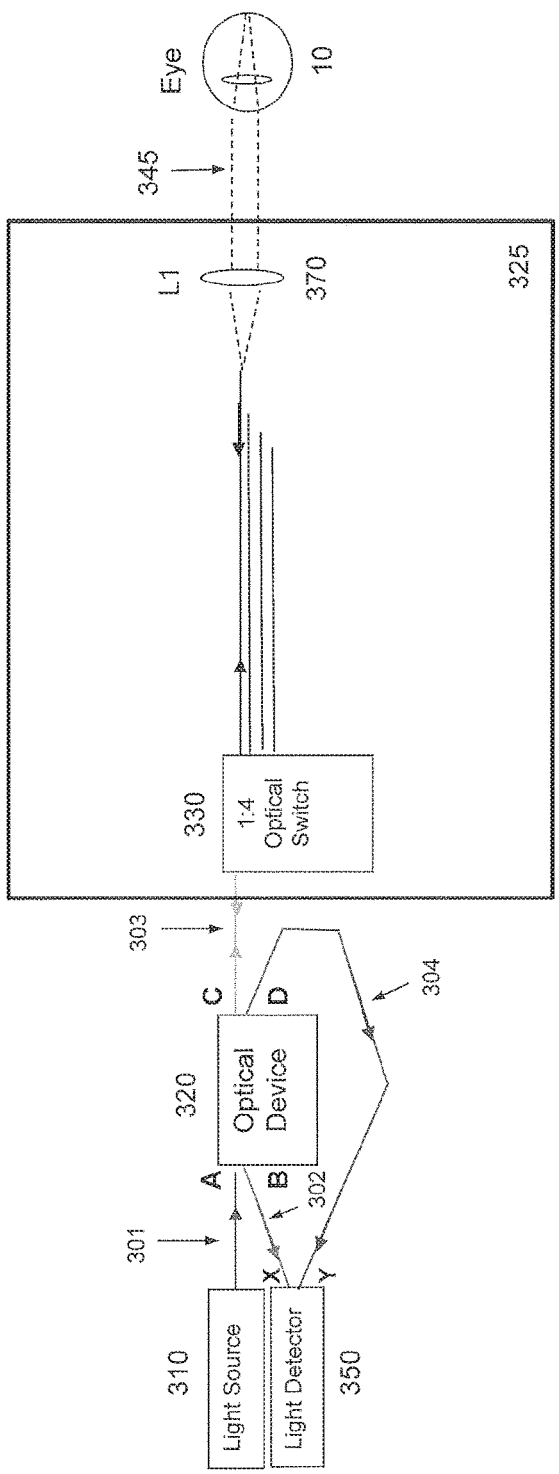
FIG. 3 is a functional block diagram of one embodiment of an optical coherence tomography (OCT) subsystem which may be included in an optical measurement system.

FIG. 3 is a functional block diagram of one embodiment of an optical coherence tomography (OCT) subsystem 300 which may be one embodiment of OCT subsystem 190 included in optical measurement system 100 and/or 200.

OCT subsystem 300 includes a light source 310, an optical device 320, a multi-focal delay line (MFDL) 325, and a light detector 350.

In some embodiments, light source 310 may comprise a superluminescent diode (SLD). In some embodiments, light source 310 may be a swept light source. In some embodiments, light source 310 may emit light at a center frequency at or near 1060 nm.

As illustrated in FIG. 3, optical device 320 is a four port device, with ports A, B, C and D labeled in FIG. 3. In some embodiments, optical device 320 may be a beam combining element, here also referred to as an "optical coupler"—for example a plate beam splitter, a beam splitting cube, or fiber optic coupler.

Multi-focal delay line 325 includes an optical switch 330 and a positive lens 370.

In some embodiments, optical switch 330 may comprise a fiber optic switch. In some embodiments, optical switch 330 may comprise a microelectromechanical systems (MEMS) switch. In some embodiments, optical switch 330 may comprise an electro-optical switch. In some embodiments, optical switch 330 may be realized via a photonic integrated circuit (PIC) or integrated optical circuit.

Figure 4B:
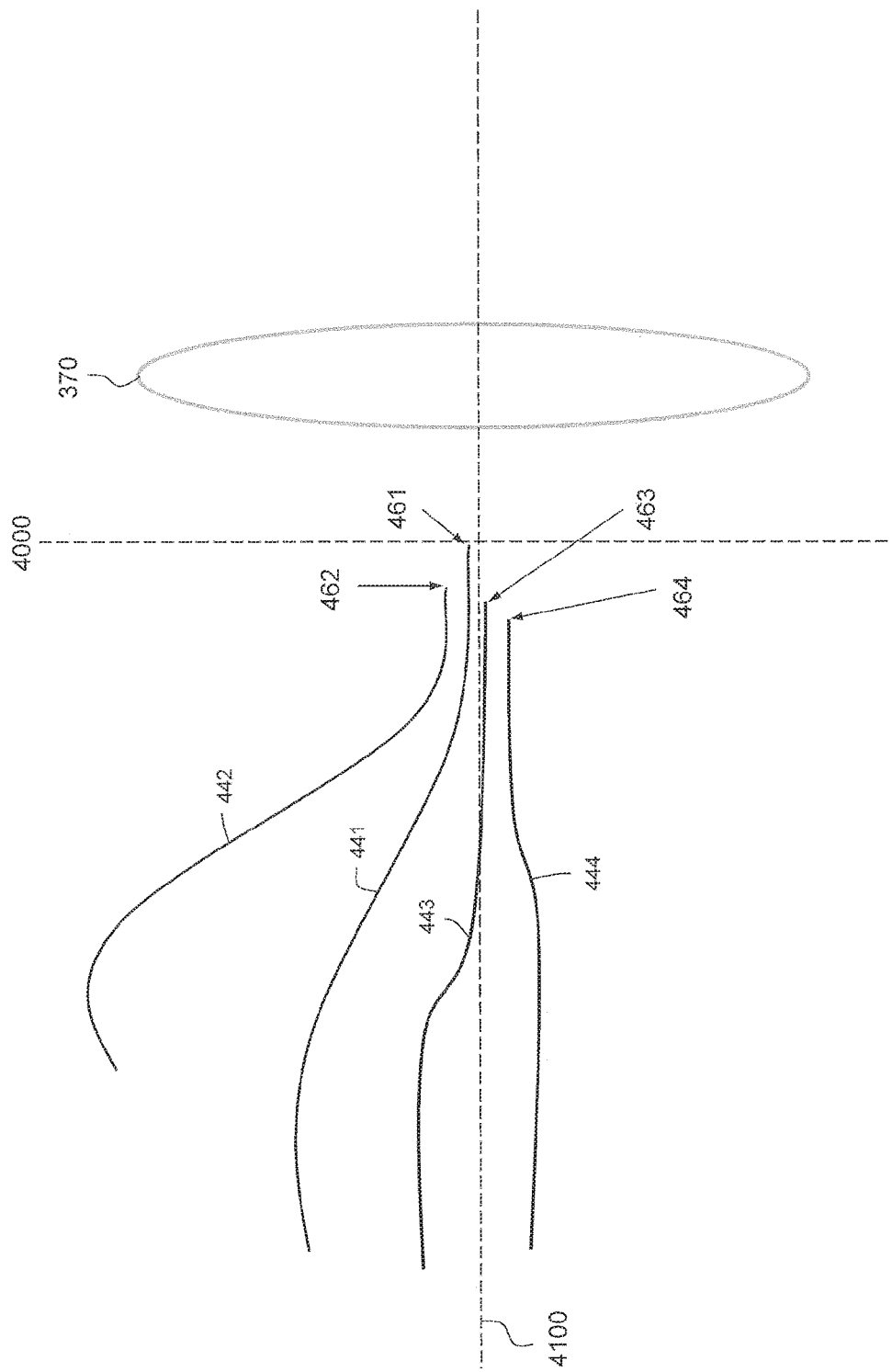

FIGS. 4A and 4B illustrate one embodiment of a multi-focal delay line (MFDL) 400 which may be included in an optical coherence tomographer, such as OCT subsystem 300 of FIG. 3. That is, MFDL 400 may be one embodiment of MFDL 325 of FIG. 3.

As shown in FIG. 4A, MFDL 400 includes optical switch 330 and positive lens 370. Optical switch 330 has an input 432 and a plurality of outputs 434 each coupled to a first end of a corresponding optical fiber 441, 442, 443 and 444. For reasons that will be explained below, each of the optical fibers 441, 442, 443 and 444 may have a corresponding different length, which can be obtained, for example, by loops of fiber 451, 452 and 454.

As illustrated in FIG. 4B, each of the optical fibers 441, 442, 443 and 444 has a corresponding second end which forms a light interface 461, 462, 463 and 464, respectively. Each of the light interfaces 461, 462, 463 and 464 is located a corresponding different distance from a back focal plane 4000 of positive lens 370 and is oriented parallel to an optical axis 4100 of positive lens 370. Beneficially, light interfaces 461, 462, 463 and 464 are all arranged near optical axis 4100. In some embodiments, light interfaces 461, 462, 463 and 464 are all arranged within about 3 degrees of optical axis 4100.

Further details of embodiments of light detector 350 will be provided below.

An example operation of an optical coherence tomographer OCT subsystem 300 will now be described with respect to FIG. 5, wherein it is assumed that MFDL 325 is embodied by MFDL 400 of FIGS. 4A-B. In the description to follow, it will be assumed that optical device 320 is an optical coupler, for example a fiber optic coupler. However it will be understood that in other embodiments optical device 320 may have a different structure or configuration while still providing the functionality as described below.

Turning back to FIG. 3, light 301 from light source 310 is provided to first port "A" of optical coupler 320. In response to light 301 received from light source 310, optical coupler 320 outputs sample light at port "C" to a sample optical path 303 and outputs reference light at port "D" to a reference optical path 304.

Light detector 310 has a pair of inputs, labeled "X" and "Y" in FIG. 3, and the reference light output from port "D" of optical coupler 320 is provided to the input "Y" of light detector 350 via reference optical path 304. In some embodiments, reference optical path 304 from port "D" of optical coupler 320 to the input "Y" of light detector 350 may include a variable optical attenuator (VOA) and/or a delay element which are not shown in FIG. 3 to simplify the illustration. In some embodiments, the delay element may be a variable delay element, for example a variable air-gap delay.

Meanwhile, the sample light 303 output at port "C" of optical coupler 320 is provided to input 432 of optical switch 330. Optical switch 330 is controlled via one or more control inputs 433 to selectively provide the light received at input 432 to one of the light interfaces 461, 462, 463 and 464 via a selected optical fiber among optical fibers 441, 442, 443 and 444.

The sample light is provided from the selected one of the light interfaces 461, 462, 463 and 464 to positive lens 370, which may be part of a positive lens system including other optical components such as other filters, lenses, etc. not shown in FIGS. 3 and 4A-B.

Positive lens 370 directs sample light 345 to eye 10, for example through an optical system not shown in FIG. 3, which may include the pair of scanning mirrors 660 for scanning the sample light 345 in two orthogonal directions on eye 10.

As noted above, each of the light interfaces 461, 462, 463 and 464 is disposed or located at a different distance from back focal plane 4000 of positive lens 370. By selecting a particular light interface 461, 462, 463 or 464 in response to a control signal received (for example from processor(s) 160) at control input 433, optical switch 330 provides sample light 345 to positive lens 370 to be directed to measure a different region of eye 10.

Figure 5:
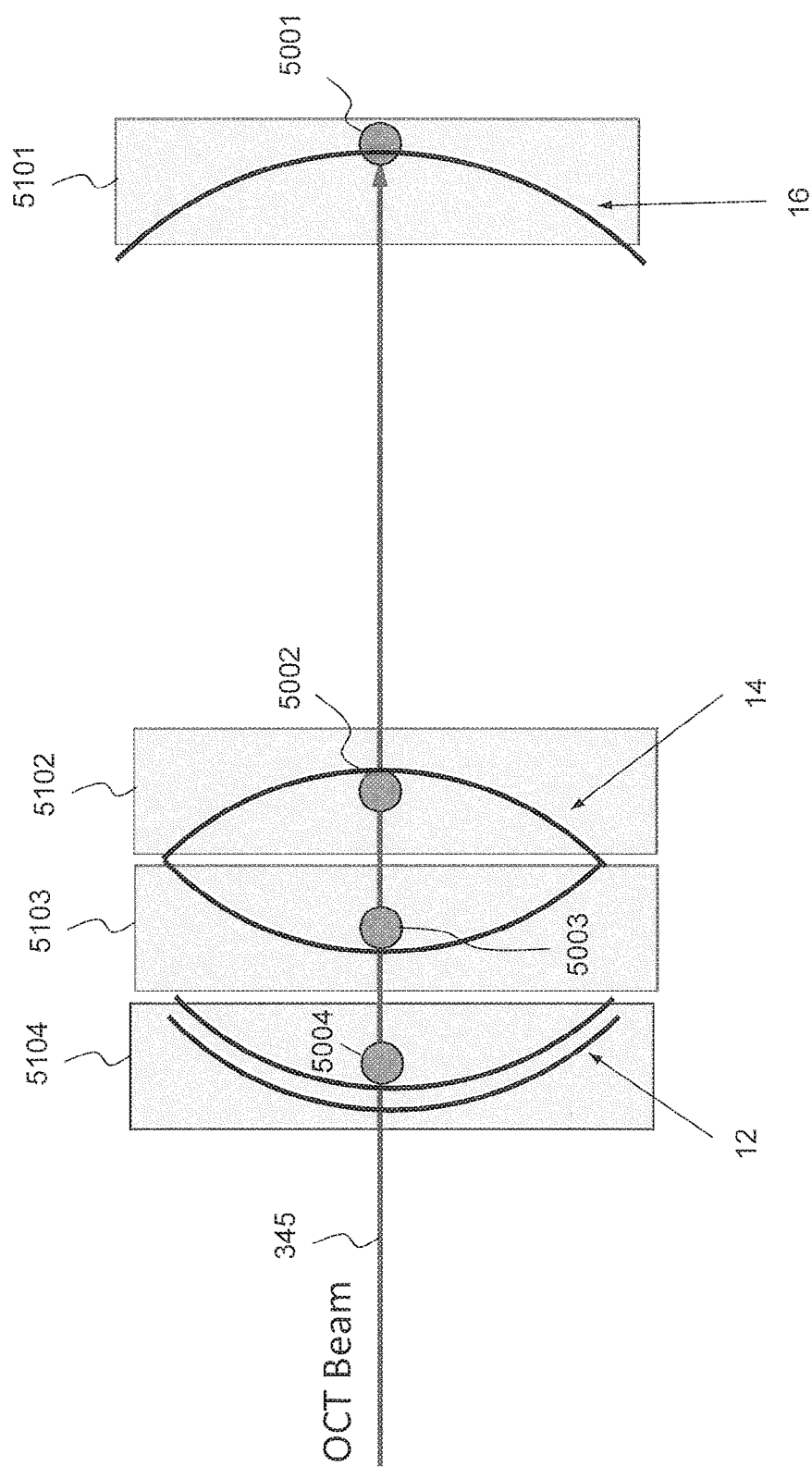
FIG. 5 illustrates operation of an optical coherence tomography (OCT) subsystem which includes an MFDL.

FIG. 5 illustrates different features or regions of eye 10 which may be measured or characterized by OCT subsystem 300. In particular, FIG. 5 shows a first region 5101, a second region 5102, a third region 5103, and a fourth region 5104 of eye 10. First region 5101 generally corresponds to a region including retina 16 of eye 10; second region 5102 generally corresponds to a region including a posterior surface of lens 14 of eye 10; third region 5103 generally corresponds to a region including an anterior surface of lens 14 of eye 10, and fourth region 5104 generally corresponds to a region including cornea 12 of eye 10.

Although FIG. 5 shows four regions, in general eye 10 may be divided into any convenient number of regions to be measured or characterized by an MFDL having a corresponding number of light interfaces. In some embodiments, the regions may span the entire depth of eye 10. Beneficially, the depth of each region may be matched to the coherence length of sample light 345 produced by light source 310. That is, the depth of each region may be less than the coherence length of sample light 345. For example, in some embodiments, each region has a depth of 4-7 mm.

In operation, MFDL 400 allows OCT subsystem 300 to selectively measure or characterize any of the regions 5101, 5102, 5103 and 5104 of eye 10 by directing sample light 345 to corresponding focus positions 5001, 5002, 5003 and 5004.

For example, in FIG. 4B it is seen that light interface 461 is located at back focal plane 4000. Accordingly, when optical switch 330 is controlled to select light interface 461 and provide the sample light to light interface 461, then positive lens 370 outputs sample light 345 as a light beam (e.g., a substantially collimated light beam) toward eye 10. In that case, the collimated beam may be focused by the optical power of eye 10 onto focus position 5001 in first region 5101 on the retina 16 of eye 10. In operation, while optical switch 330 is controlled to select light interface 461, scanning mirrors 660 may be controlled (e.g., by a control signal from processor(s) 160) to scan the sample light in two dimensions (e.g., an x direction and an orthogonal y direction) to obtain measurements at a number of focal points in region 5101. In some embodiments, scanning mirrors 660 may be controlled to make at least four measurements in region of interest 5104. In some embodiments, scanning mirrors 660 may be controlled to make up to 100 measurements in region of interest 5101. In some embodiments, an additional number of light interfaces may be included in the system to adapt the focus and optical delay of the system to cover the complete range of strongly myopic, myopic, near emmetropic, hyperopic and strongly hyperopic eyes.

On the other hand, when optical switch 330 is controlled to select light interface 464 and provide the sample light to light interface 464, then positive lens 370 may produce sample light 345 as a converging light beam focused on cornea 12 in region 5104 of eye 10.

Similarly, when optical switch 330 is controlled to select light interfaces 462 and 463, respectively, then positive lens 370 may produce sample light 345 as a converging light beam focused on the posterior and anterior surfaces, respectively, of lens 14 of eye 10 in regions 5102 and 5103, respectively.

Beneficially, optical switch 330 has a relatively rapid switching time. For example, when optical switch 330 is a MEMS device, then the switching time may be on the order of a few milliseconds. When optical switch 330 is based on an electro-optic switch, then the switching time may be even faster. Through the use or rapid optical switching technologies, in some embodiments OCT measurements may be made for all regions of interest of eye 10 in less than 80 msec, which may prevent eye motion during the measurement interval from diminishing or degrading the quality of the OCT measurements.

When optical switch 330 is controlled to select light interface 461 and provide the sample light to light interface 461, then the sample light is scattered and/or reflected by retina 16 in region 5101 of eye 10. This scattered and/or reflected light, referred to here as "return light," passes in the backwards direction back through positive lens 370 and impinges on light interface 461, through which it is coupled back to optical switch 330 via optical fiber 441. The return light then passes back through optical switch 330 to port "C" of optical coupler 320. Optical coupler 320 passes the return light via return path 302 to port "B" from which it is provided to input "X" of light detector 350.

Light detector 350 detects one or more interference signal between the return light received at port "X" and the reference light received at port "Y." Data representing the detected interference signal may be provided from light detector 350 to processor(s) 160 for measuring one or more characteristics of region 5101 of eye 10, for example including retina 16 of eye 10.

Meanwhile, when optical switch 330 is controlled to select light interface 464 and provide the sample light to light interface 464, then the sample light is scattered and/or reflected by cornea 12 in region 5104 of eye 10 and is returned in the backwards direction as return light to positive lens 370. The return light passes back through positive lens 370 and impinges on light interface 464, through which it is coupled back to optical switch 330 via optical fiber 444. The return light then passes back through optical switch 330 to port "C" of optical coupler 320. Optical coupler 320 passes the return light to port "B" from which it is provided via return path 303 to input "X" of light detector 350, and the resulting interference signal(s) with the reference light are detected.

Similarly, when optical switch 330 is controlled to select light interfaces 462 and 463, respectively, then the sample light is scattered and/or reflected by the posterior and anterior surfaces, respectively, of lens 14 in regions 5102 and 5103, respectively, of eye 10, and returned back to positive lens 370. The return light passes back through optical fibers 442 and 443, respectively, to optical switch 330, port "C" of optical coupler 320, and input "X" of light detector 350 as discussed above.

Beneficially, the lengths of optical fibers 441, 442, 443 and 444 are all different from each other so that the delays through the sample path for each of the corresponding regions 5101, 5102, 5103 and 5104 are matched to the delay through reference path 304. As explained above, the delays can be obtained, for example, by loops of fiber 451, 452 and 454. Thus, beneficially, the same optical switch 330 which is used to select a different light interface for each region of the eye also selects a corresponding delay to be added to match the delay in reference optical path 304.

When retina 16 is being measured, then the sample light 345 has to pass through a depth of eye 10 from lens 14 to retina 16 which may have dispersion characteristics similar to water, which sample light 345 does not pass through when cornea 12 is being measured, yielding different dispersion characteristics. Accordingly, in some embodiments, two or more (e.g., all) of the optical fibers 441, 442, 443 and 444 may have different dispersions to match the dispersions in the path through eye 10 to the particular regions which are being measured via selection of those particular optical fibers and their corresponding light interfaces. The condition of matching the dispersion and/or the optical delay increases the strength of the interference signal.

As described above, MFDL 400 includes a 1:4 optical switch 330 creating four channels and four corresponding light interfaces 461, 462, 463 and 464 for measuring four corresponding measurement regions 5101, 5102, 5103 and 5104 of an object to be measured (e.g., eye 10). This configuration is convenient when, for example, an OCT subsystem is employed to measure or characterize four different regions of an object being measured, such as cornea 12, anterior and posterior surfaces of lens 15, and retina 16 of eye 10. However in general it will be understood that an OCT subsystem including an MFDL as described above may have more or less than four channels with more of less than four light interfaces for measuring more or less than four corresponding measurement regions of an object to be measured (e.g., eye 10).

As described above, OCT subsystem 300 may measure one or more characteristics of eye 10, including measuring a length or distance between different features of eye 10 (e.g., between any combination of: cornea 12, anterior and posterior surfaces of lens 14, and retina 16) based on interference signals detected by light detector 350 when different ones of the light interfaces 461, 462, 463 and 464 are selected, for example by processor(s) 160.

Figure 6:
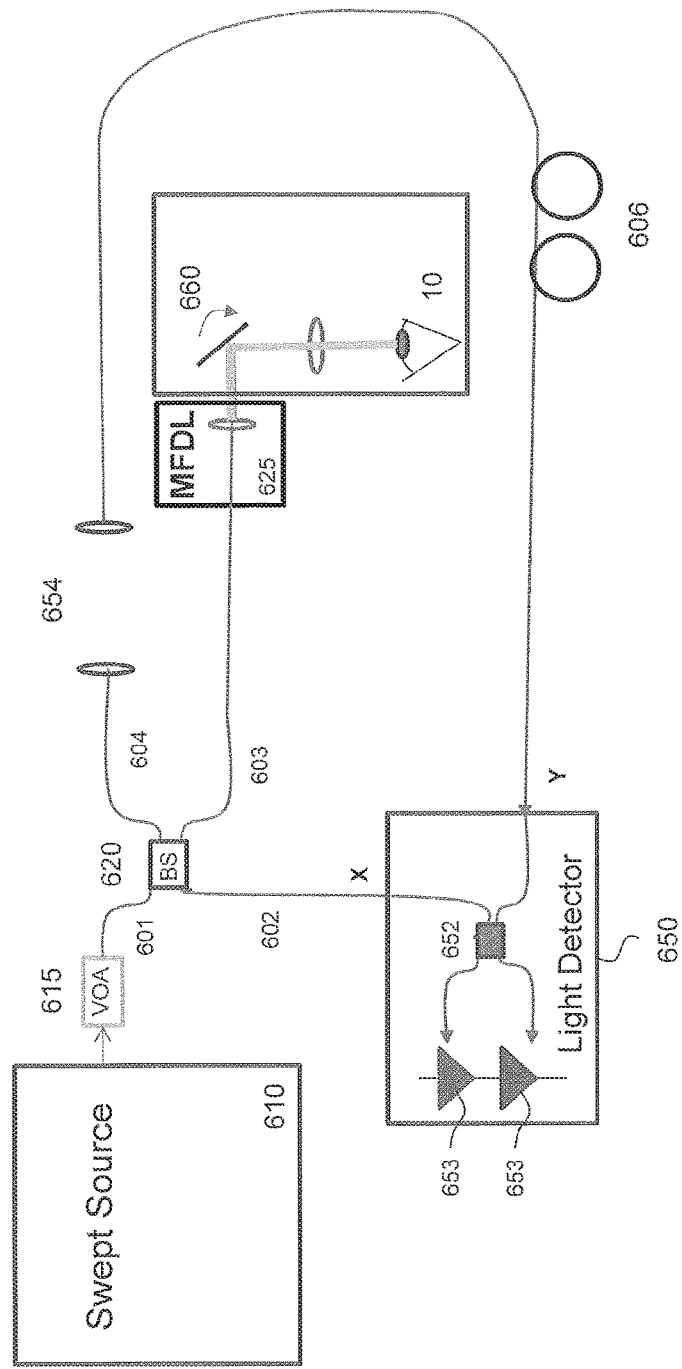
FIG. 6 is a functional block diagram of another embodiment of an optical coherence tomography (OCT) subsystem which may be included in an optical measurement system.

FIG. 6 is a functional block diagram of another embodiment of an optical coherence tomography (OCT) subsystem 600 that may be included in an optical measurement system, such as optical measurement system 100 or optical measurement system 200. OCT subsystem 600 may be one example embodiment of OCT subsystem 300 illustrated in FIG. 3.

OCT subsystem 600 includes a light source 610, a beam splitter 620, a multi-focal delay line (MFDL) 625, and a light detector 650. Light source 610, beam splitter 620, and multi-focal delay line (MFDL) 625 may have the same configurations, respectively, as light source 310, beam splitter 320, and multi-focal delay line (MFDL) 325 described above with respect to FIG. 3. MFDL 400 illustrated in FIGS. 4A and 4B may be one embodiment of MFDL 625 of FIG. 6.

FIG. 6 shows return optical path 602, sample optical path 603 and reference optical path 604 through which the return light, sample light and reference light, respectively pass.

OCT subsystem 600 also includes polarization paddles 606 for adjusting the light polarization of the reference light in reference optical path 604, and a variable optical attenuator (VOA) 615 for adjusting the amplitude of light 601 output by light source 610.

FIG. 6 also explicitly shows scanning mirrors 660 and an air gap 654 serving as a delay (e.g., an adjustable or variable delay) in reference optical path 604.

FIG. 6 also illustrates in more detail an example embodiment of light detector 650, which may be one embodiment of light detector 350 in FIG. 3. Light detector 650 includes a beam splitter 652 and a pair of detector elements 653 (e.g., photodiodes). Beneficially, beam splitter 652 is a 50/50 beam splitter.

In operation, beam splitter 652 combines the return light received at input "X" with the reference light at input "Y" to create the interference signal, which is distributed equally to both output legs beam splitter 652, which are in turn connected to the pair of detector elements 653. The 50/50 beam splitter 652 has the property that although both output legs contain the same interference signal, the interference signals are 180 degrees out of phase with respect to each other. These interference signals create photo currents in detector elements 653, which are configured as a "balanced photodetector." That is, detector elements 653 are stacked on each other with the current output formed by the difference in photo currents in the two detector elements 652. This difference may generally be picked off between the detector elements 653. Thus, the pair of detector elements 653 arranged this way removes the common mode intensity (background noise) and isolates the interference fringes. As a result, the interference signal is captured with comparatively little background noise.

Figure 7:
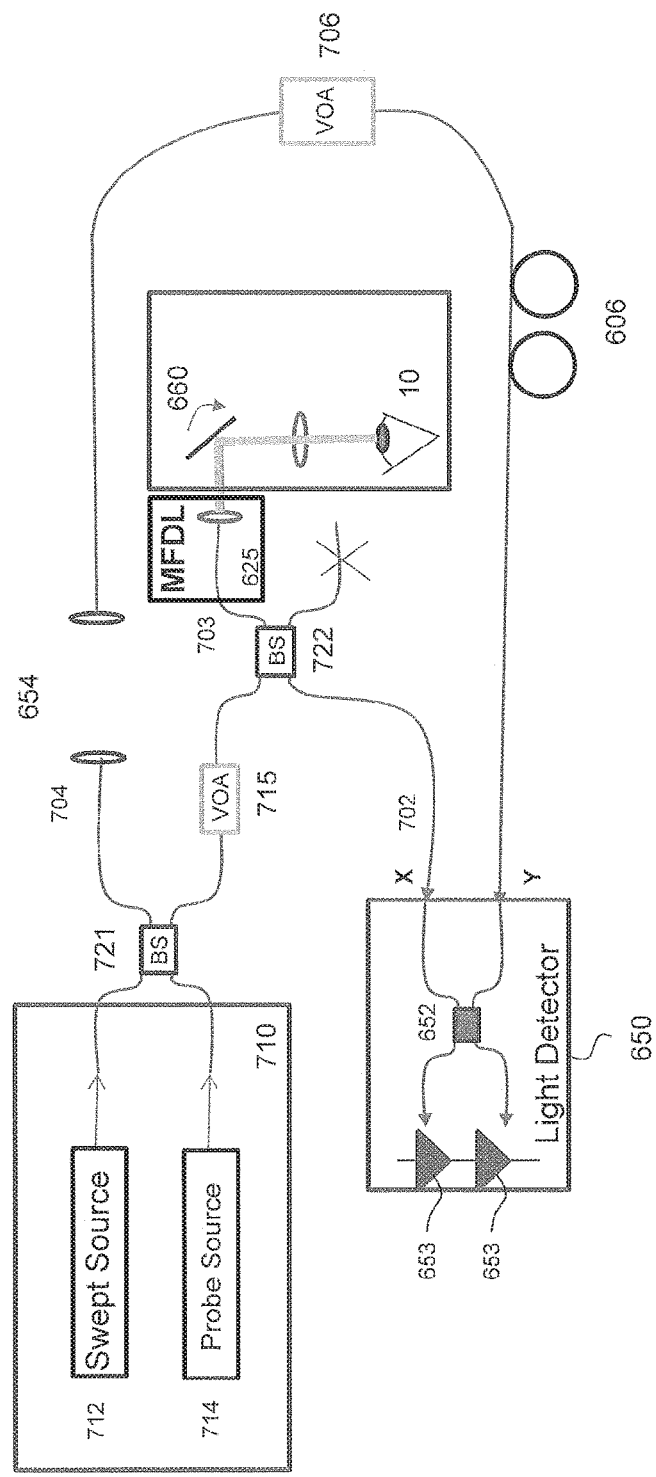
FIG. 7 is a functional block diagram of yet another embodiment of an optical coherence tomography (OCT) subsystem which may be included in an optical measurement system.

FIG. 7 is a functional block diagram of yet another embodiment of an optical coherence tomography (OCT) subsystem 700 that may be included in an optical measurement system such as optical measurement system 100 or optical measurement system 200. OCT subsystem 700 may be another example embodiment of OCT subsystem 300 illustrated in FIG. 3.

OCT subsystem 700 is similar to OCT subsystem 600—especially in operation—and only differences therebetween will be highlighted. OCT subsystem 700 includes a light source 710, a first beam splitter 721, a second beam splitter 622, multi-focal delay line (MFDL) 625, and light detector 650. Multi-focal delay line (MFDL) 625 and light detector 650 have been described above with respect to FIG. 6, and, again, MFDL 400 illustrated in FIGS. 4A and 4B may be one embodiment of MFDL 625 of FIG. 7.

Light source 710 includes swept source 712 and a probe source 714. First beam splitter 721 combines the light from swept source 712 and a probe source 714 and outputs reference light to reference path 704 and sample light to second beam splitter 722 through a first VOA 715. Second beam splitter 722 receives the sample light and couples it to sample optical path 703. Second beam splitter 722 also receives return light from eye 10 via MFDL 625 and provides the return light to light detector 650 via return optical path 702.

OCT subsystem 700 also includes a second VOA 706 in the reference optical path 704.

Otherwise, the construction and operation of OCT subsystem 700 is the same as for OCT subsystem 600, and the details thereof will not be repeated.

Figure 8:
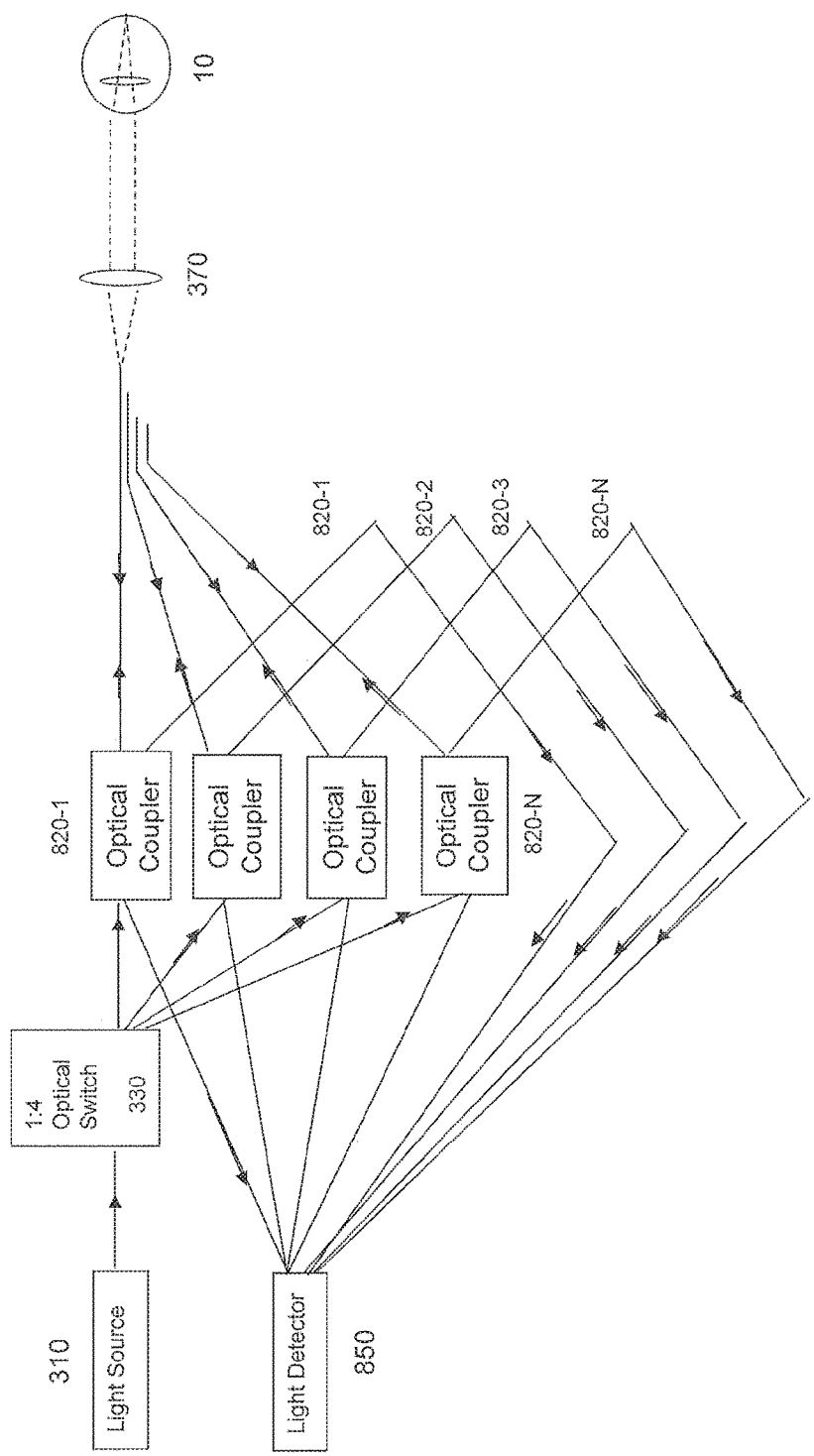
FIG. 8 is a functional block diagram of still another embodiment of an optical coherence tomography (OCT) subsystem which may be included in an optical measurement system.

FIG. 8 is a functional block diagram of still another embodiment of an optical coherence tomography (OCT) subsystem 800 that may be included in an optical measurement system, such as optical measurement system 100 or optical measurement system 200. OCT subsystem 800 differs principally from OCT subsystems 300, 600 and 700 in that OCT subsystem 800 includes a plurality of "interferometer legs" in the return optical path and the sample optical path.

More specifically, OCT subsystem 800 includes N (e.g., N=4) optical couplers 820-1 . . . 820-N disposed in optical paths between optical switch 330 and positive lens 370. Each of the optical couplers 820-1 . . . 820-N includes: a first port coupled to an output of optical switch 330; a second port coupled to a corresponding return light input of light detector 850; a third port coupled to a corresponding one of a plurality of light interfaces (e.g., light interfaces 461, 462, 463 or 464 of FIG. 4); and a fourth port. A plurality of reference optical paths 804-1, 804-2, 804-3 and 804-N are each coupled between the fourth port of a corresponding one of the plurality of optical couplers 820-1 . . . 820-N, and a corresponding reference light input of light detector 850. In general, OCT subsystem 800 may include additional elements, such as variable optical attenuators and scanning mirrors—such as scanning mirrors 660 of FIG. 6. For simplicity of illustration, such elements are not shown in FIG. 8.

Light detector 850 has a plurality of sample light inputs each coupled to a second port of a corresponding one of the optical couplers 820-1 . . . 820-N, and a corresponding plurality of reference light inputs each coupled to an output of a corresponding one of the reference optical paths 804-1, 804-2, 804-3 and 804-N. In some embodiments, light detector may include a plurality of beam splitters such as beam splitter 652, each coupled to one of the sample light inputs and a corresponding one of the reference light inputs. The outputs of all of the beam splitters may be provided in close proximity to a common pair of detector elements, such as detector elements 653 of FIG. 6, and detection may then proceed as described above with respect to FIG. 6.

In operation, it should be understood that due to the operation of optical switch 330, only one of the sample light inputs and a corresponding one of the reference light inputs will actively supply sample light and reference light to light detector 850 at any time.

When measuring eye 10 with OCT subsystem 800, different layer in retina 16 may have different intensities of scatter back into OCT subsystem 800 for different polarizations. So making measurements with different polarizations can reveal different details of retinal anatomy and disease conditions. Accordingly, in some embodiments, OCT subsystem 800 may include one or more polarization control elements, such as polarization paddles, which may individually optimize the polarization of the return light, and/or the reference light in each reference optical paths 804-1, 804-2, 804-3 and 804-N, for different parts of eye 10.

Figure 9:
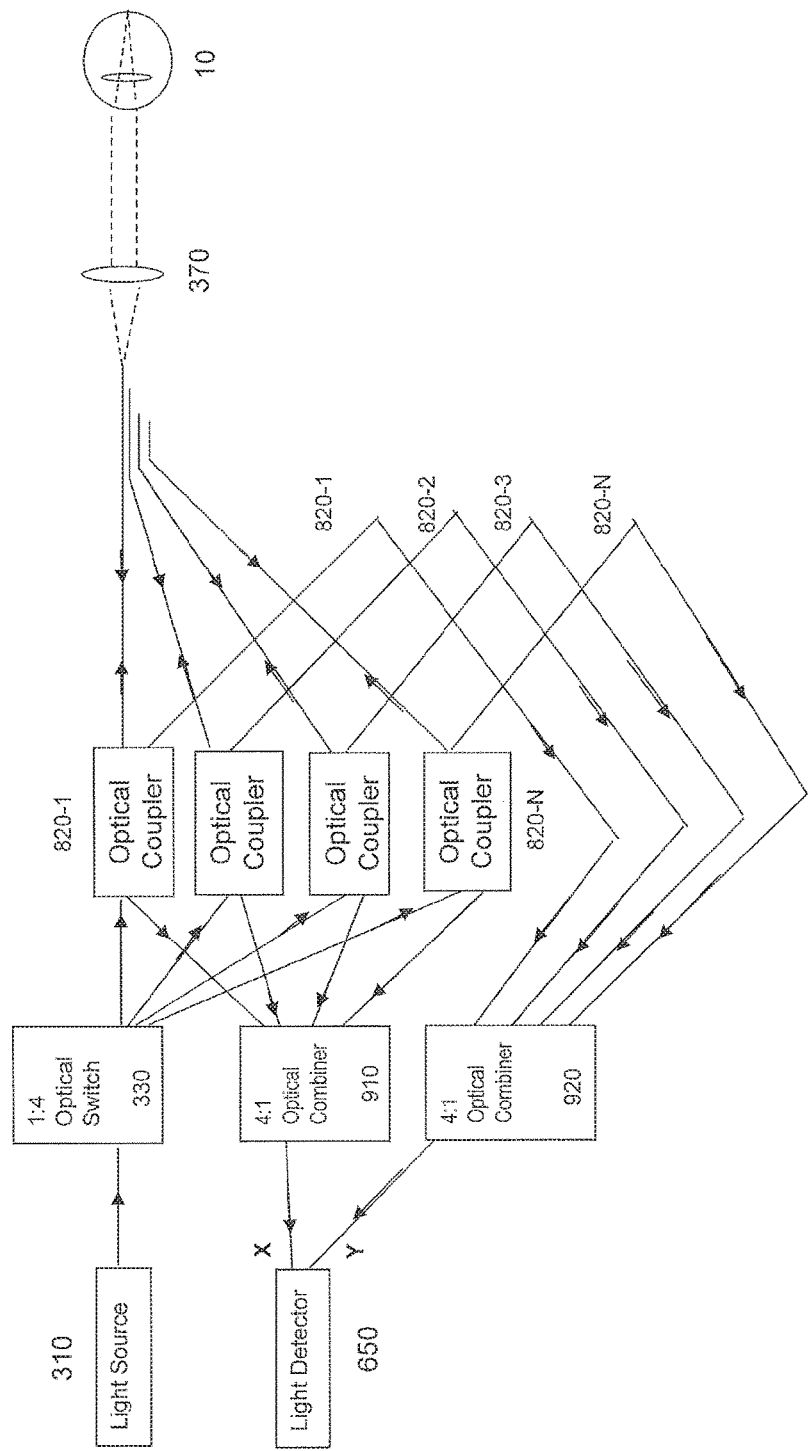
FIG. 9 is a functional block diagram of a further embodiment of an optical coherence tomography (OCT) subsystem which may be included in an optical measurement system.

FIG. 9 is a functional block diagram of a further embodiment of an optical coherence tomography (OCT) subsystem 900 that may be included in an optical measurement system, an optical measurement system such as optical measurement system 100 or optical measurement system 200. OCT subsystem 900 is similar to OCT subsystem 800 and only differences therebetween will be highlighted. OCT subsystem 900 includes: a first optical combiner 910 having a plurality of inputs each of which is coupled to the second port of a corresponding one of the plurality of optical couplers 820-1 . . . 820-N, and having an output coupled to the first light input ("X") of light detector 650; and a second optical combiner 920 having a plurality of inputs each of which is coupled to on output of a corresponding one of the plurality of reference optical paths 804-1 . . . 804-N, and having an output coupled to the second light input ("Y") of light detector 650. In some embodiments, first and second optical combiners 910 and 920 may each comprise a fiber optic fuser. The addition of first and second optical combiners 910 and 920 may simplify the design of the light detector compared to light detector 850 of OCT subsystem 800.

Figure 10:
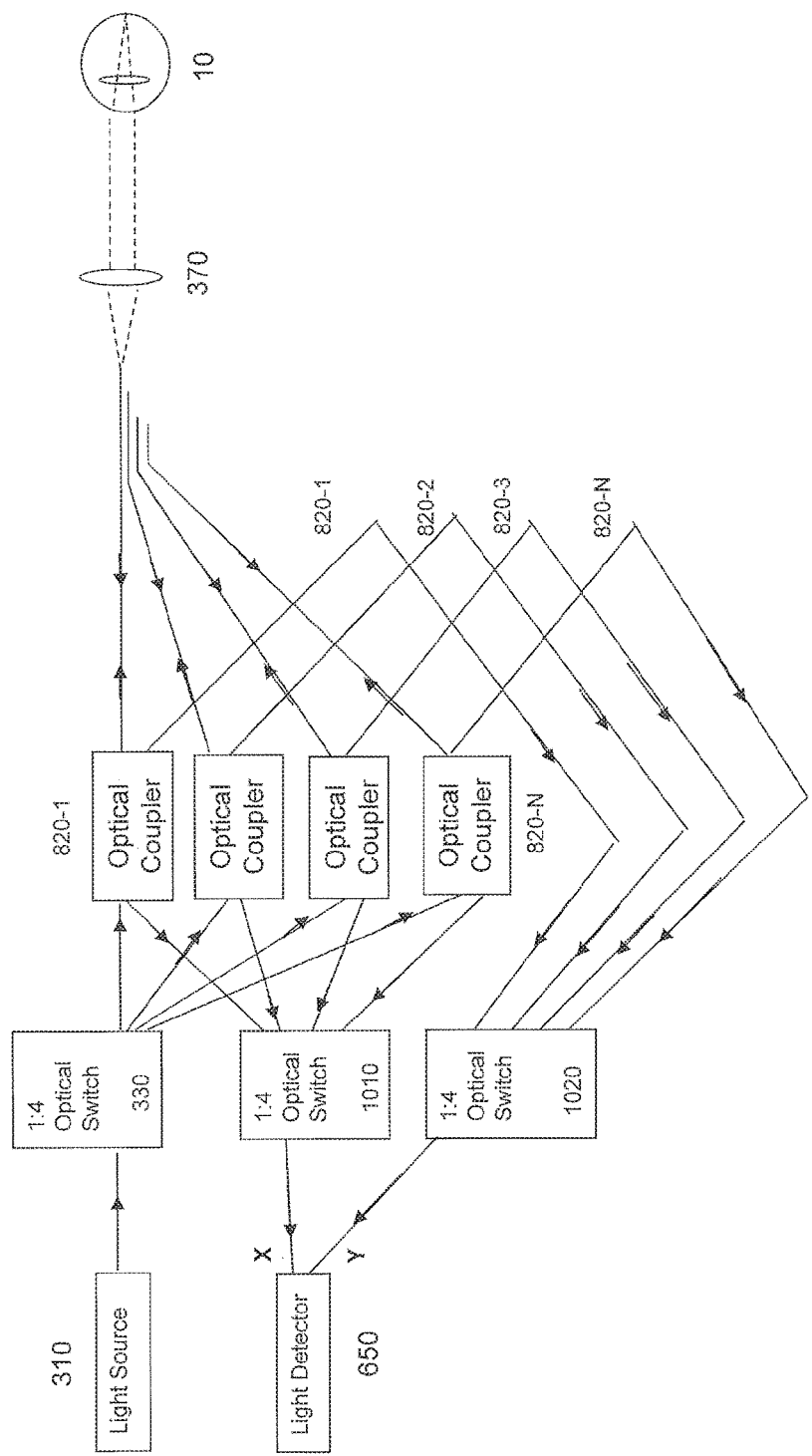
FIG. 10 is a functional block diagram of still a further embodiment of an optical coherence tomography (OCT) subsystem which may be included in an optical measurement system.

FIG. 10 is a functional block diagram of still a further embodiment of an optical coherence tomography (OCT) subsystem 1000 that may be included in an optical measurement system, an optical measurement system such as optical measurement system 100 or optical measurement system 200. OCT subsystem 1000 is similar to OCT subsystem 900 and only differences therebetween will be highlighted. In place of first and second optical combiners 910 and 920, OCT subsystem 1000 includes a second optical switch 1010 having a plurality of inputs each of which is coupled to the second port of a corresponding one of the plurality of optical couplers 820-1 . . . 820-N, and having an output coupled to the first light input of light detector 650; and a third optical switch 1020 having a plurality of inputs each of which is coupled to on output of a corresponding one of the plurality of reference optical paths 804-1 . . . 801-N, and having an output coupled to the second light input of light detector 650. Second and third optical switches 1010 and 1020 may be controlled to be switched in conjunction with the switching of optical switch 330.

Figure 11:
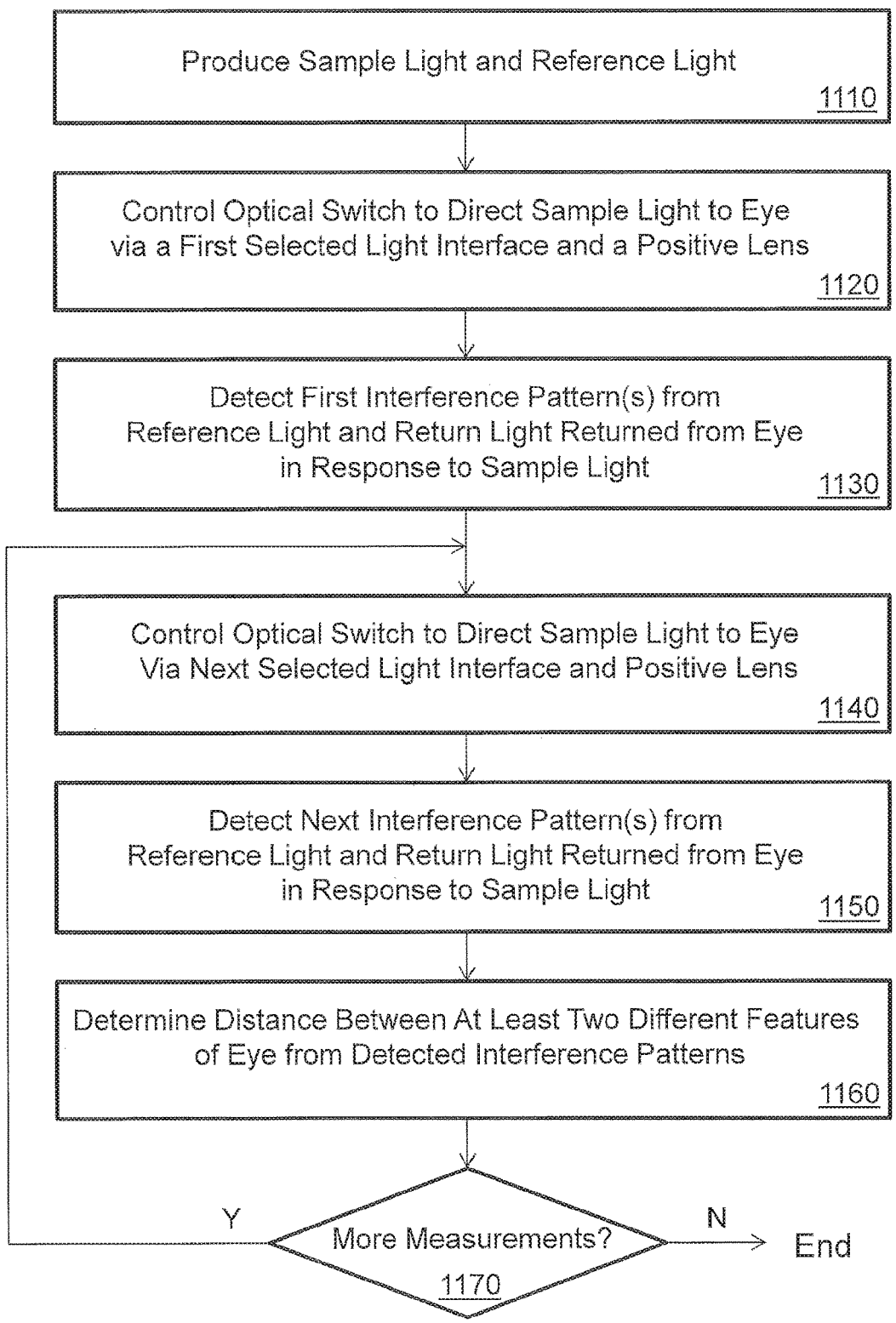
FIG. 11 is a flowchart of an example embodiment of a method of measuring an optical characteristic of an eye.

FIG. 11 is a flowchart of an example embodiment of a method 1100 of measuring one or more optical characteristics of an eye.

In an operation 1110, an optical measurement system including an OCT subsystem produces sample light and reference light.

In an operation 1120, the optical measurement system controls an optical switch to direct the sample light to an object being measured (e.g., an eye), via a first selected light interface and a positive lens.

In an operation 1130, the optical measurement instrument detects one or more first interference signal(s) from the reference light and return light returned from the eye in response to the sample light being provided via the first light interface. For example, a scanning mirror may direct the sample light to a plurality of different focal points in a selected first region of the eye while the sample light is provided to the eye via the selected first light interface and the positive lens, and a first interference signal may be detected for each of the focus points in the first region of the eye.

In an operation 1140, the optical measurement system controls the optical switch to direct the sample light to an object being measured (e.g., an eye), via a next (e.g., second) selected light interface and the positive lens.

In an operation 1150, the optical measurement instrument detects one or more next (e.g., second) interference signal(s) from the reference light and return light returned from the eye in response to the sample light being provided via the second light interface. For example, a scanning mirror may direct the sample light to a plurality of different focal points in a selected second region of the eye while the sample light is provided to the eye via the selected second light interface and the positive lens, and a second interference signal may be detected for each of the focus points in the second region of the eye.

In an operation 1160, an optical measurement system determines the distance between at least two different features of the eye from the detected interference signals. For example, the optical measurement instrument may determine: the distance between the cornea and the anterior surface of the lens, determine the distance between the anterior surface of the lens and the posterior surface of the lens (i.e., thickness of the lens), determine the distance between the posterior surface of the lens and the retina, determine the distance between the cornea and the retina, etc.

In an operation 1170, it is determined whether more measurements should be made, in which case the process returns to operation 1140. Otherwise, the measurement operation ends.

All patents and patent applications cited herein are hereby incorporated by reference in their entirety.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention. As used herein, the terms first and second are used to describe structures and methods without limitation as to the order of the structures and methods which can be in any order, as will be apparent to a person of ordinary skill in the art based on the teachings provided herein.

While certain illustrated embodiments of this disclosure have been shown and described in an exemplary form with a certain degree of particularity, those skilled in the art will understand that the embodiments are provided by way of example only, and that various variations can be made without departing from the spirit or scope of the invention. Thus, it is intended that this disclosure cover all modifications, alternative constructions, changes, substitutions, variations, as well as the combinations and arrangements of parts, structures, and steps that come within the spirit and scope of the invention as generally expressed by the following claims and their equivalents.

We claim:

1. A system, comprising:
    a light source configured to emit light;
    a first optical system configured to receive the light from the light source and to produce therefrom reference light and sample light;
    a reference optical path configured to receive the reference light from the first optical element;
    a plurality of light interfaces;
    an optical switch configured to receive the sample light from the first optical system and to selectively couple the sample light to a selected light interface among the plurality of light interfaces;
    a positive lens system;
    wherein the light interfaces are all separated and spaced apart from the positive lens system and located at different distances than each other from an effective focal plane of the positive lens system, wherein the positive lens system is configured to receive the sample light from the selected light interface, to provide the sample light to an eye, to receive return light from the eye, and to provide the return light to the selected light interface,
        wherein the optical switch is further configured to provide the return light to the first optical system;
    a light detector configured to receive the reference light from the reference optical path, and to receive the return light from the first optical system, and in response thereto to detect at least one interference signal; and
    one or more processors configured to control the optical switch to selectively couple the sample light to each of the plurality of light interfaces, one at a time, and further configured to measure at least one characteristic of the eye from the detected interference signals when the sample light is selectively coupled to the plurality of light interfaces.

2. The system of claim 1, wherein the optical switch has a plurality of output ports, and wherein the system includes a plurality of optical waveguides each connected to one of the output ports, the plurality of optical waveguides providing the plurality of light interfaces.

3. The system of claim 2, wherein each of the light interfaces comprises a second end of a corresponding one of the optical waveguides.

4. The system of claim 1, wherein the one or more processors are further configured to determine at least one distance between two different areas of the eye from the detected interference signals when the sample light is selectively coupled to the light interfaces.

5. The system of claim 4, where the at least one distance includes at least one of: a distance between a reference plane and the anterior surface of a cornea, a distance between a surface of a cornea and a surface of a lens, a distance between a surface of the lens and a retina; and a distance between a surface of the cornea and the retina.

6. The system of claim 1, wherein at least one of the light interfaces is distanced from the positive lens so that the sample light provided from the optical system to the eye is substantially focused on the retina.

7. The system of claim 6, wherein at least another one of the light interfaces is distanced from the positive lens so that the sample light provided from the optical system to the eye is substantially focused on a cornea of the eye.

8. The system of claim 6, wherein at least another one of the light interfaces is distanced from the positive lens so that the sample light provided from the optical system to the eye is substantially focused on a lens of the eye.

9. The system of claim 1, wherein the light produced by the light source has a coherence length, and wherein the light interfaces are arranged with respect to the focal plane of the positive lens system such that the return light from the eye for a first one of the light interfaces principally comes from a first depth in the eye and the return light from the eye for a second one of the light interfaces principally comes from a second depth in the eye different from the first depth, and wherein a distance between the first depth and the second depth is greater than the coherence length.

10. The system of claim 9, wherein the system is further configured to automatically change a delay provided by the multi-focal delay line to match each of the first and second depths when the light is output from the first one of the light interfaces and the second one of the light interfaces, respectively.

11. The system of claim 1, wherein the light interfaces are all disposed within three degrees of an optical axis of the positive lens system.

12. The system of claim 1, wherein the first optical system includes one of a fiber optic coupler and a beam splitter configured to receive the light from the light source and to produce therefrom the reference light and the sample light.

13. A method, comprising:
    producing sample light and reference light from a common light source;

controlling an optical switch to direct the sample light to an eye via a first selected light interface and a positive lens;

detecting at least one first interference signal from the reference light and return light returned from the eye in response to the sample light being directed to the eye via the first selected light interface;

controlling the optical switch to direct the sample light to the eye via a second selected light interface and the positive lens, wherein the second selected light interface is disposed at a different distance from a focal plane of the positive lens than the first selected light interface;

detecting at least one second interference signal from the reference light and return light returned from the eye in response to the sample light being directed to the eye via the second selected light interface; and determining at least one distance between at least two different features of the eye from the detected first and second interference signals.

14. The method of claim 13, wherein the first selected light interface is distanced from the positive lens so that the sample light provided to the eye is substantially collimated.

15. The method of claim 14, wherein the second selected light interface is distanced from the positive lens so that the sample light is focused on a cornea of the eye.

16. The method of claim 15, further comprising determining a distance between the cornea and a retina of the eye from the detected first and second interference signals.

17. The method of claim 13, further comprising scanning the sample light in at least one direction so as to create a plurality of first interference signals from the reference light and return light returned from the eye in response to the sample light being directed to the eye via the first selected light interface and to create a plurality of second interference signals from the reference light and return light returned from the eye in response to the sample light being directed to the eye via the second selected light interface.

18. A system, comprising:
a light source;
a positive lens having a focal plane;
a plurality of light interfaces each located a corresponding different distance from the focal plane of the positive lens;
an optical switch configured to receive a light from the light source and to selectively direct sample light to the positive lens via a selected one of the plurality of light interfaces, wherein the positive lens is further configured to direct the sample light to an object to be measured; and
a light detector configured to receive the return light returned from the object to be measured in response to the sample light being directed to the object to be measured via the positive lens, and to receive a reference light produced from the light from the light source, and in response thereto to detect at least one first interference signal.

19. The system of claim 18, further comprising a controller configured to:
control the optical switch to direct the sample light to the positive lens via the first selected one of the plurality of light interfaces to create the first interference signal from the reference light and return light returned from the object to be measured in response to the sample light being directed to the object to be measured via the first light interface;

control the optical switch to direct the sample light to the positive lens via a second selected one of the plurality of light interfaces to create at least one second interference signal from the reference light and return light returned from the object to be measured in response to the sample light being directed to the object to be measured via the second light interface; and determine at least one distance between at least two different features of the object to be measured from the first and second interference signals.

20. The system of claim 18, further comprising:
a plurality of optical couplers, each optical coupler including:
a first port coupled to an output of the optical switch,
a second port coupled to a corresponding return light input of the light detector,
a third port coupled to a corresponding one of the plurality of light interfaces, and
a fourth port; and
a plurality of reference optical paths each coupled between the fourth port of a corresponding one of the plurality of optical couplers and a corresponding reference light input of the light detector.

21. The system of claim 18, further comprising:
a plurality of optical couplers, each optical coupler including:
a first port coupled to an output of the optical switch,
a second port coupled to a first light input of the light detector,
a third port coupled to a corresponding one of the plurality of light interfaces,
and
a fourth port; and
a plurality of reference optical paths each coupled between the fourth port of a corresponding one of the plurality of optical couplers and a second light input of the light detector.

22. The system of claim 21, further comprising:
a first optical combiner having a plurality of inputs each of which is coupled to the second port of a corresponding one of the plurality of optical couplers, and having an output coupled to the first light input of the light detector; and
a second optical combiner having a plurality of inputs each of which is coupled to on output of a corresponding one of the plurality of reference optical paths, and having an output coupled to the second light input of the light detector.

23. The system of claim 21, further comprising:
a second optical switch having a plurality of inputs each of which is coupled to the second port of a corresponding one of the plurality of optical couplers, and having an output coupled to the first light input of the light detector; and
a third optical switch having a plurality of inputs each of which is coupled to on output of a corresponding one of the plurality of reference optical paths, and having an output coupled to the second light input of the light detector.

* * * * *